United States Patent [19]
Sandison et al.

[11] Patent Number: 5,920,399
[45] Date of Patent: Jul. 6, 1999

[54] MULTISPECTRAL IMAGING METHOD AND APPARATUS

[75] Inventors: David R. Sandison, Moriarty; Mark R. Platzbecker; Timothy D. Vargo, both of Albuquerque, all of N. Mex.; Randal R. Lockhart, Lorain, Ohio; Michael R. Descour, Tucson, Ariz.; Rebecca Richards-Kortum, Austin, Tex.

[73] Assignee: Sandia Corporation, Albuquerque, N.M.

[21] Appl. No.: 08/820,298

[22] Filed: Mar. 18, 1997

[51] Int. Cl.$^6$ .......................... G01N 21/25; G01N 21/64; G01J 3/30; F21K 2/00
[52] U.S. Cl. .......................... 356/418; 356/417; 356/318; 356/416; 250/461.1; 250/462.2; 600/591
[58] Field of Search .......................... 600/591; 356/318, 356/301, 417, 418; 250/461.1, 462.2

[56] References Cited

U.S. PATENT DOCUMENTS

| | | |
|---|---|---|
| 3,945,371 | 3/1976 | Adelman . |
| 4,477,190 | 10/1984 | Liston et al. .............................. 356/418 |
| 5,421,339 | 6/1995 | Ramanujam et al. . |
| 5,424,543 | 6/1995 | Dombrowski et al. .................. 250/330 |
| 5,450,857 | 9/1995 | Garfield et al. . |
| 5,670,113 | 9/1997 | Akong et al. ........................ 356/418 X |

OTHER PUBLICATIONS

Anita Mahadevan, Michele Follen Mitchell, Elvio Silva, Sharon Thomsen and Rebecca R. Richards–Kortum, Study of the Fluorscence Properties of Normal and Neoplastic Human Cervical Tissue, Lasers in Surgery and Medicine 13:647–655 (1993).

N. Ramanujam, M. F. Mitchell, A. Mahadevan, S. Warren, S. Thomsen, E. Silva and R. Richards–Kortum, In vivo diagnosis of cervical intraepithelial neoplasia using 337–nm–excited laser–induced fluorescence, Proc. Natl. Acad. Sci. USA, vol. 91, pp. 10192–10197, Oct. 1994, Medical Sciences.

*Primary Examiner*—Frank G. Font
*Assistant Examiner*—Roy M. Punnoose
*Attorney, Agent, or Firm*—V. Gerald Grafe

[57] ABSTRACT

A multispectral imaging method and apparatus adapted for use in determining material properties, especially properties characteristic of abnormal non-dermal cells. A target is illuminated with a narrow band light beam. The target expresses light in response to the excitation. The expressed light is collected and the target's response at specific response wavelengths to specific excitation wavelengths is measured. From the measured multispectral response the target's properties can be determined. A sealed, remote probe and robust components can be used for cervical imaging

17 Claims, 5 Drawing Sheets

MULTISPECTRAL IMAGING METHOD AND APPARATUS

This invention was made with Government support under Contract DE-AC0494AL85000 awarded by the U.S. Department of Energy. The Government has certain rights in the invention.

BACKGROUND OF THE INVENTION

This invention relates to the field of determining cell properties from multispectral imaging of the cells' response to incident light.

Cervical cancer usually develops along a junction where two types of cervical cells meet. This junction changes during a woman's lifetime, as one cell type is transformed into another. The cells' DNA is accessed for this cellular transformation, increasing the chance for mutations that can lead to cancer. The cancer begins as a pre-cancerous lesion; if left untreated the lesion can deepen over time to become an invasive cancer. Other cell abnormalities have similar pre-cancerous development phases.

The conventional way to screen for cervical cancer is the Pap smear. In a Pap smear, a sample of cells is taken from the cervix and analyzed under a microscope by an expert (a cytotechnologist). Pap smear results are typically available after about one week. Pap smear analysis can generate from 10% to 50% false negative results and false positive results. A positive Pap smear result usually triggers a second Pap smear. A second positive Pap smear prompts a colposcopic examination, in which the cervix is examined with a low power microscope by a professional colposcopist. The colposcopic examination, like many methods for detecting cancerous and pre-cancerous cells, required that part of the tissue be biopsied. Less invasive methods and apparatus that can detect cell abnormalities could improve the quality of care and simultaneously reduce the cost.

Abnormal cells can display different light emission characteristics than normal cells. Many researchers have attempted to detect abnormal cells based on this difference. Garfield and Glassman, U.S. Pat. No. 5,450,857, tried to detect changes in cervical connective tissue associated with changes in cervical dilation or effacement. Their method illuminated the cervix with laser light of a selected wavelength, then measured fluorescent emissions. Their method could not provide information about response to multiple excitation wavelengths or differentiate among responses at different wavelengths or from different parts of the cervix. Accordingly, their method could not provide enough information to detect cell abnormalities.

Adelman, U.S. Pat. No. 3,945,371, described an apparatus for visual inspection of the interior of cavities with access only through restricted orifices. Adelman's invention comprised a fiberoptic probe and a low power light source. The image of the interior was projected to a translucent display screen. Adelman's invention only provided for visual inspection; it could not and did not excite the cavity interior with selected wavelengths of light or measure the response thereto.

Ramanujam et al., U.S. Pat. No. 5,421,339, described a method for detecting abnormalities in cervical cells based on induced fluorescence intensity. Light from a Nitrogen pumped dye laser illuminated a 1 mm spot on a cervix. A full spectrum of fluorescence response from the cells in the 1 mm spot was collected. The Nitrogen pumped dye laser was pulsed to differentiate it from background light. Nitrogen pumped dye lasers can be very difficult to use and have high maintenance requirements and low reliability, making them poorly suited for clinical application. Detectors suitable for collecting a full spectrum of fluoresced light from a pulsed laser are complicated and consequently expensive. The limitation to a single 1 mm spot makes screening of large areas of the cervix impossible. Ramanujam's instrument accordingly was suited for use following Pap smear screening, but was not suitable for use instead of Pap smear screening.

Dombrowski, U.S. Pat. No. 5,424,543, described an imaging spectroradiometer. The apparatus provided a sequence of spectral images, where each spectral image depicted the scene at a selected wavelength. The apparatus, however, did not allow for excitation of a target at selected wavelengths, and did not provide for a probe that could be used for imaging hard to access targets such as the cervix. Accordingly, Dombrowski's apparatus could only provide multispectral visualization of a scene and could not be used to determine cell properties.

Other instruments have been proposed that collect fluorescence data from multiple discrete spots of the target. These systems provide some spatial information through the detection at multiple spots. They do not, however, provide full image detection and thus provide no more information than would multiple uses of an instrument like that described by Ramanujam.

Other cell properties can also be of interest. For example, NADH can provide information about cell metabolism. Present methods of measuring NADH, however, are limited to single cell, tissue removal methods. As another example, hemoglobin oxygenation can provide useful diagnostic information. Present blood gas measurement systems, however, require blood samples to be sent to a laboratory for analysis.

Accordingly, there is an unmet need for a non-invasive method and apparatus adapted for use in determining properties characteristic of cells.

SUMMARY OF THE INVENTION

The present invention provides a multispectral imaging method and apparatus adapted for use in determining cell properties. A target comprising multiple cells is illuminated with a narrow band light beam. The target cells express light in response to the excitation. The expressed light is collected and the target cells' response at specific response wavelengths to specific excitation wavelengths is measured. From the measured multispectral response the target cells' properties can be determined.

The present invention can provide determinion of target cell properties across a portion of a target surface. The excitation beam and response determinion can preserve image information so that the multispectral response of the portion of the target is measured. The present invention can employ a sealed, remote probe and robust components so that it can be adapted for use in cervical imaging.

DESCRIPTION OF THE FIGURES

The accompanying drawings, which are incorporated into and form part of the specification, illustrate embodiments of the invention and, together with the description, serve to explain the principles of the invention.

DETAILED DESCRIPTION OF THE INVENTION

The present invention provides a multispectral imaging method and apparatus adapted for use in determining cell properties.

Figure 1:
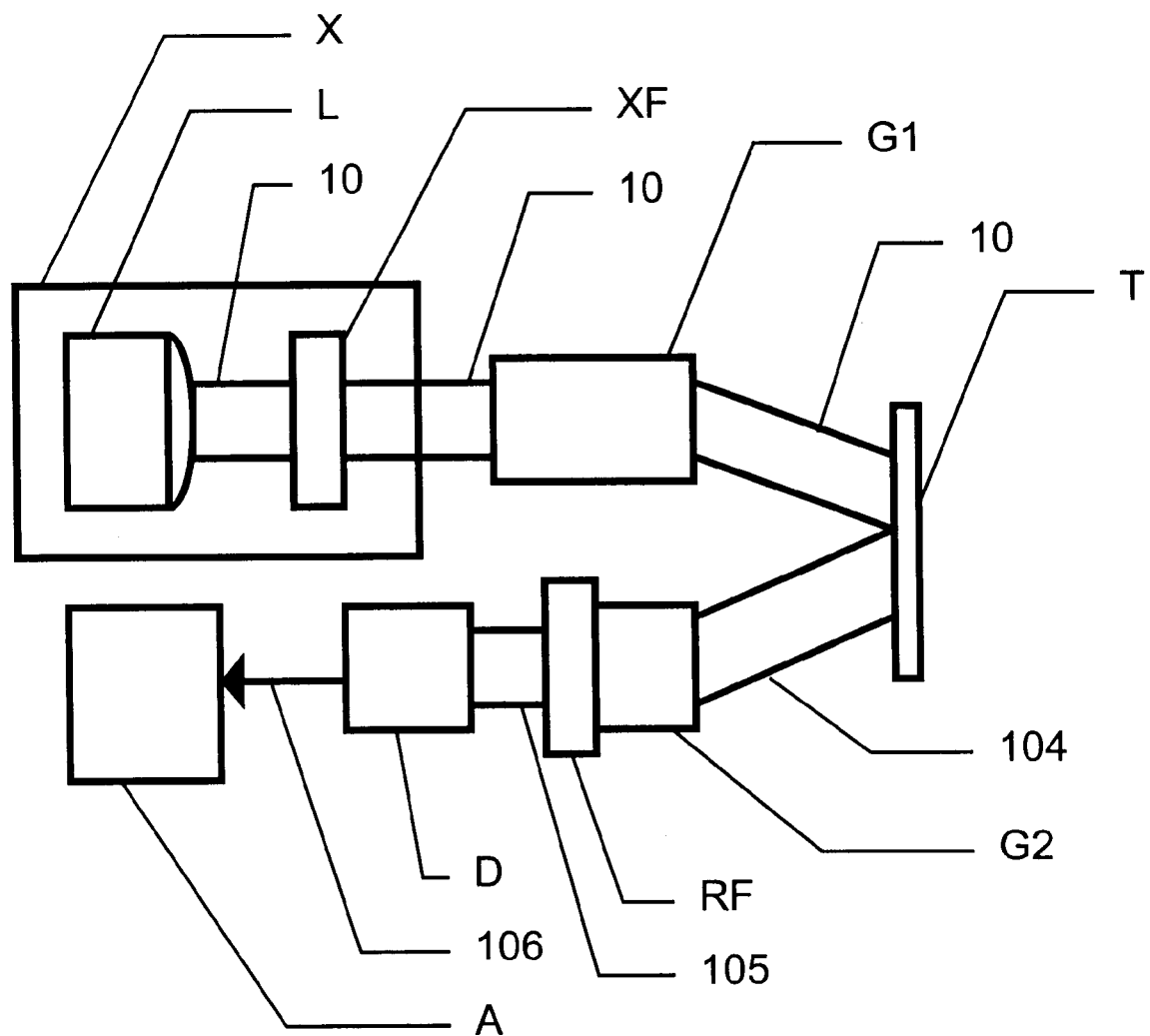
FIG. 1 is a block diagram of a multispectral imaging system according to the present invention.

FIG. 1 is block diagram of a multispectral imaging system according to the present invention. An excitation source X generates a narrow band light beam 102. Narrow band light beam 102 can comprise light with a wavelength band of 2 to 80 nanometers relative to a center wavelength. Narrow band light beam 102 can be achieved in various ways; FIG. 1 shows a broad band light source L that generates a broad band light beam 101 combined with a filter XF that transforms broad band light beam 101 to narrow band light beam 102. Filter XF can be a filter wheel, rotated to select the center wavelength of narrow band light beam 102, whose center wavelength can therefore vary with time. A computer can control the filter wheel's rotation. A first delivery means G1 directs a delivered light beam 103 to a target T. Target T can express light 104 in response to delivered light beam 103. Target T can express light in various ways, including by reflection, absorption, fluorescence, Raman scattering, and diffuse scattering. For convenience of illustration, delivered light beam 103 and expressed light 104 are shown at an angle to each other, they can be coaxial with appropriate optics. Expressed light 104 from target T can be transmitted by a second delivery means G2 to a response filter RF. Specific wavelength bands of expressed light 104 can be selected by response filter RF for analysis. Response filter RF can be a filter wheel rotated to select specific wavelengths and form a narrow band light beam 105. A detector D detects the intensity of narrow band light beam 105 and produces signal 106. Signal 106 from detector D therefore represents the target's response at a selected response wavelength to a selected excitation wavelength. Analysis means A can determine selected properties of target T from response signal 106. Example analysis techniques are described in U.S. Pat. No. 5,421,339, incorporated herein by reference, and in "In vivo diagnosis of cervical intraepithelial neoplasia using 337-nm-excited laser-induced fluorescence," Ramanujam et al., Proc. Natl. Acad. Sci. USA, vol. 91, pp. 10193–10197, incorporated herein by reference.

Figure 2:
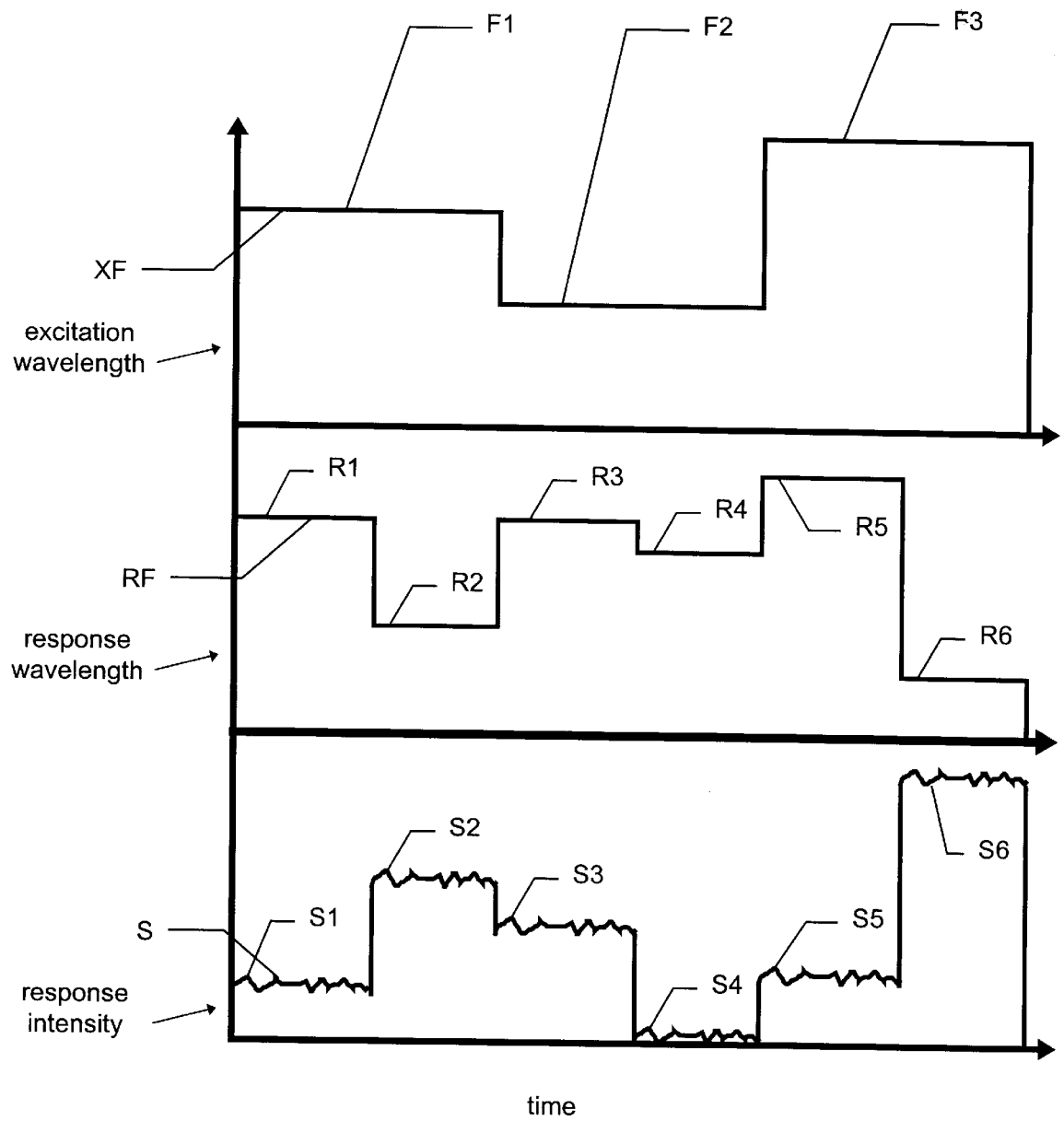
FIG. 2 is a graph of excitation wavelength, target response wavelength, and detected signal intensity as a function of time.

FIG. 2 is a graph of excitation wavelength, target response wavelength, and detected signal intensity as a function of time. Three excitation wavelengths F1, F2, F3 are shown. A target's response to excitation wavelength F1 is shown to be of interest at two response wavelengths R1, R2. The target's response to excitation wavelength F2 is shown to be of interest at two response wavelengths R3, R4. The target's response to excitation wavelength F3 is shown to be of interest at two response wavelengths R5, R6. The response wavelengths of interest can be chosen based on the spectral responsiveness of the target material. For example, wavelengths characteristic of changes in target material properties can be used. Examples of suitable wavelengths for selected target materials are discussed in "Study of the Fluorescence Properties of Normal and Neoplastic Human Cervical Tissue," Mahadevan et al., Lasers in Surgery and Medicine 13:647–655 (1993), incorporated herein by reference. The intensity of the target's response to excitation wavelength F1 at response wavelength R1 is shown as response signal intensity S1. The response at response wavelength R2 is shown as response signal intensity S2. The greater amplitude of signal intensity S2 relative to signal intensity S1 indicates that the target response to excitation wavelength F1 was greater at response wavelength R2 than at response wavelength R1. The response to excitation wavelength F2 at response wavelengths R3, R4 is shown as response signal intensities S3, S4, respectively. The target had almost no response at response wavelength R4. The response to excitation wavelength F3 at response wavelengths R5, R6 is shown as response signal intensities S5, S6, respectively. The target had a very strong response at response wavelength R6. The excitation and response wavelengths can be chosen to examine particular properties of the target. The response signal intensities Si can then be analyzed to determine the target's properties where varying properties change the target response to the excitation wavelengths Fi at the response wavelengths Ri.

Figure 3:
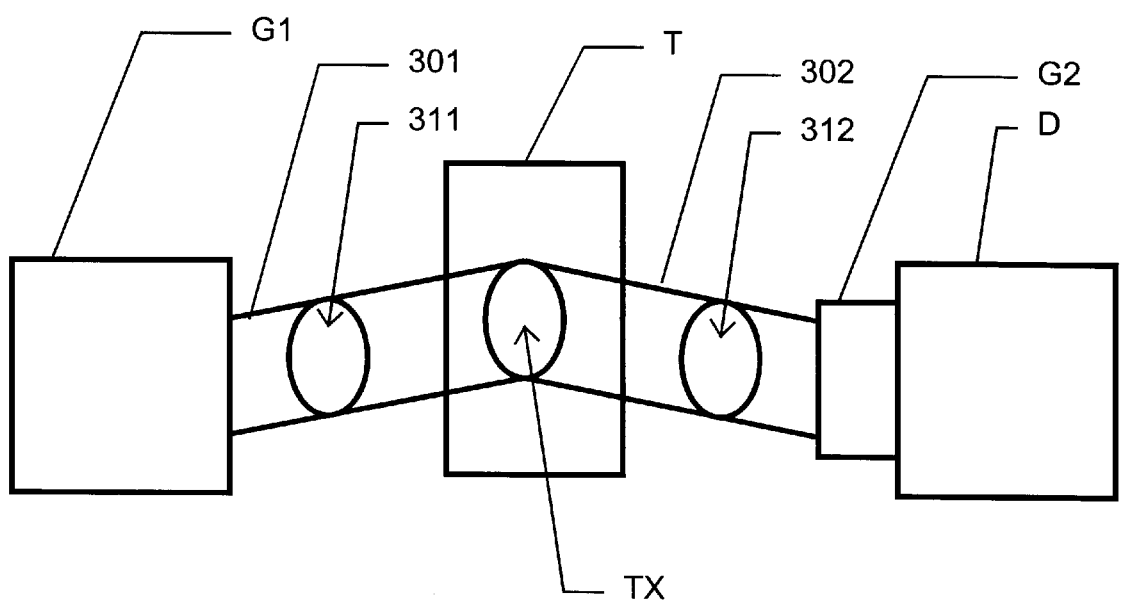
FIG. 3 is a representation of part of a multispectral imaging system according to the present invention.

FIG. 3 is a representation of part of a multispectral imaging system according to the present invention. Light beam 301 delivered to a target T by a first delivery means G1 has a cross section 311. A portion TX of a surface of target T is therefore excited by light beam 301. Light 302 expressed by portion TX of target T can be collected so that the collected light 302 also has a cross section 312, corresponding to an image of portion TX of target T excited. Second delivery means G2 delivers expressed light 302 to a detector D. Detector D can generate a signal representative of the intensity at a plurality of points in cross section 312 and thereby preserve the image information. An image of the response of portion TX of target T excited can thus be obtained, providing information about the response of a specific portion TX of target T. This additional information can allow, for example, a clinically relevant portion of a cervix to be screened at one time, allowing the present apparatus to provide similar information as traditional Pap smear screening.

Figure 4:
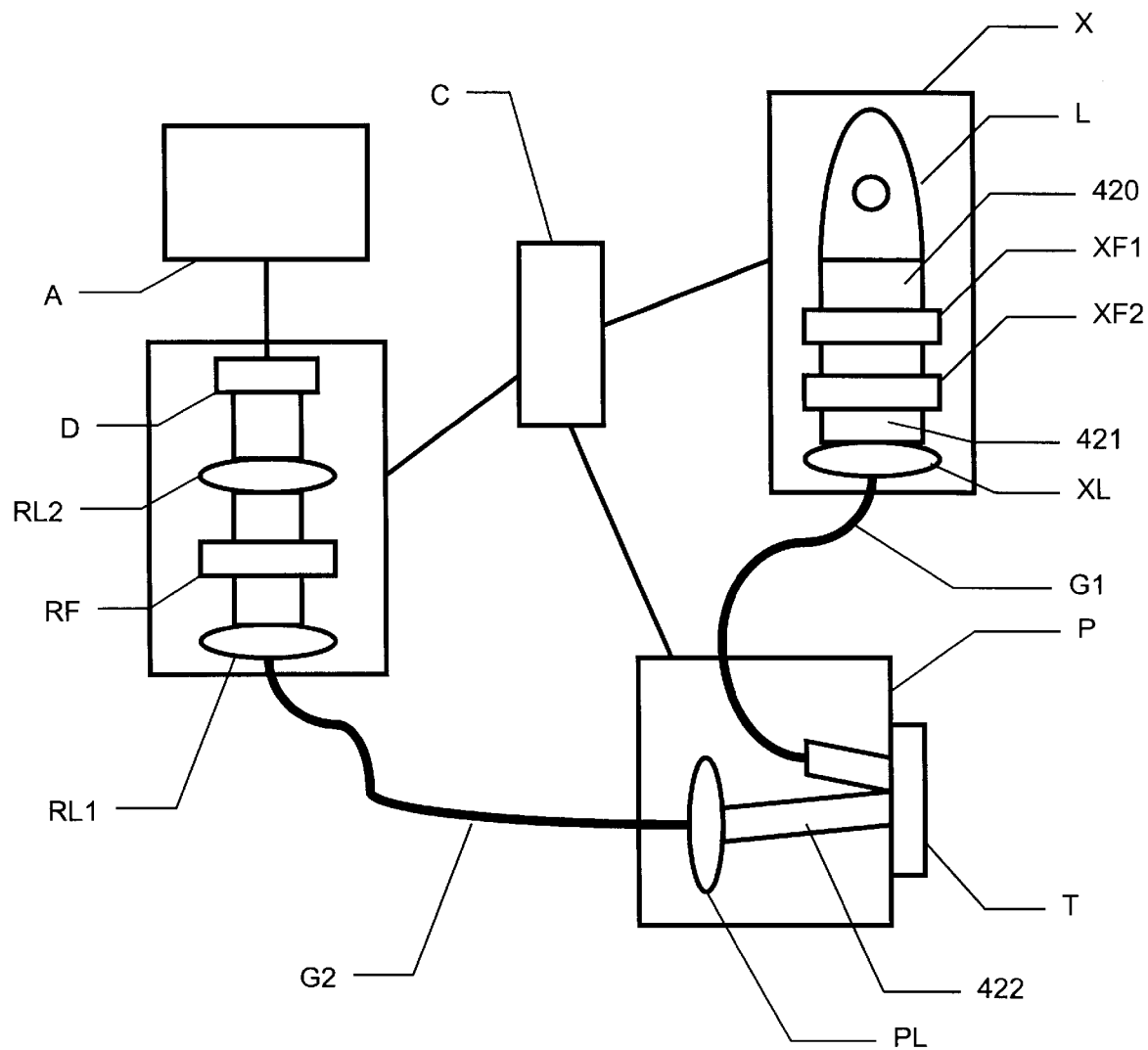
FIG. 4 is a block diagram of a multispectral imaging system according to the present invention.

FIG. 4 is a block diagram of a multispectral imaging system according to the present invention. An excitation source X comprises a lamp L, two filters XF1, XF2, and a lens XL. For imaging an entire cervix in one to ten seconds, lamp L can deliver about 10 mW power at each excitation wavelength and the wavelength selection time can be about one second. As an example, a 300 W xenon arc lamp with a built-in parabolic reflector can deliver over 40 mW/nm output power in the wavelength range from 300 nm to 2000 nm. The parabolic reflector can collect light more efficiently than condensor/reflector geometries. Integrating the reflector into the lamp can also obviate the alignment problems that accompany conventional lamp housings.

Interference filters can select wavelengths from the parabolic reflector's nearly collimated output. Filter XF1 can be an infrared filter to reject heat energy in the light beam 420 output of lamp L. Filter XF1 can remove near infrared light (approximately from 800 nm to 2000 nm) that could otherwise heat and damage other parts of the apparatus. As an example, KG1 glass such as that made by Schott Glass Technologies of Duryea, Pa., can be used as filter XF1. KG1 glass absorbs strongly in the near infrared, and dissipates the energy as heat. A KG1 filter XF1 can be radially symmetric and can be aligned along the optic axis of lamp L.

Filter XF2 can be a filter wheel, controlled by a controller C to select specific excitation wavelengths for target excitation. Interference filters with bandwidths on the order of 10 nm can be used. Filter XF2 preferably does not fluoresce or otherwise emit light that might be confused with light 422 expressed by a target T. Filter XF2 preferably adequately blocks light outside the pass band, which can be from 200 nm to 2000 nm wide.

A light beam 421 from the filters XF1, XF2 can be focused into a first delivery means G1 by lens XL. A condenser lens can be used as lens XL. A liquid light guide is an example of a suitable first delivery means G1. The liquid light guide can have an input aperture approximately 3 mm in diameter to avoid alignment problems common to small diameter optical fibers. First delivery means G1 delivers the light energy to a probe P adapted for illuminating a target T. Preferably, probe P is sealed against outside light energy or contaminants that can disturb the light beams or introduce light that can be confused with light 422 expressed by target T.

Light 422 expressed by target T can be focused into a second delivery means G2 by lens PL. Imaging lenses can be used for lens PL. Second delivery means G2 preferably preserves the cross section of the light 422 expressed by target T. A coherent optical fiber bundle is an example of a suitable second delivery means G2. The fiber density in the bundle must be high enough to preserve the image. The fibers in the bundle also must transmit the wavelengths of interest.

Light from second delivery means G2 can be focused by lens RL1 onto a filter RF. Lens RL1 can collimate the real image transmitted by a coherent optical fiber bundle. Filter RF can be a filter wheel, controlled by controller C, to select specific response wavelengths of interest in the target's response. Light from filter RF can be focused onto a detector D by lens RL2. Detector D preferably preserves the cross section information of the light 422 expressed by target T. A CCD imaging detector is an example of a suitable detector D. A CCD imaging detector converts photons to an analog voltage proportional to the integrated intensity at each pixel, where each pixel corresponds to a portion of the image focused onto the detector D. Detector D can output signals representative of the target's response 422 at specific response wavelengths to excitation by light of specific excitation wavelengths. The signals from the detector D can be used by analysis means A to determine target properties, including detection of cell abnormalities, as discussed above.

Figure 5:
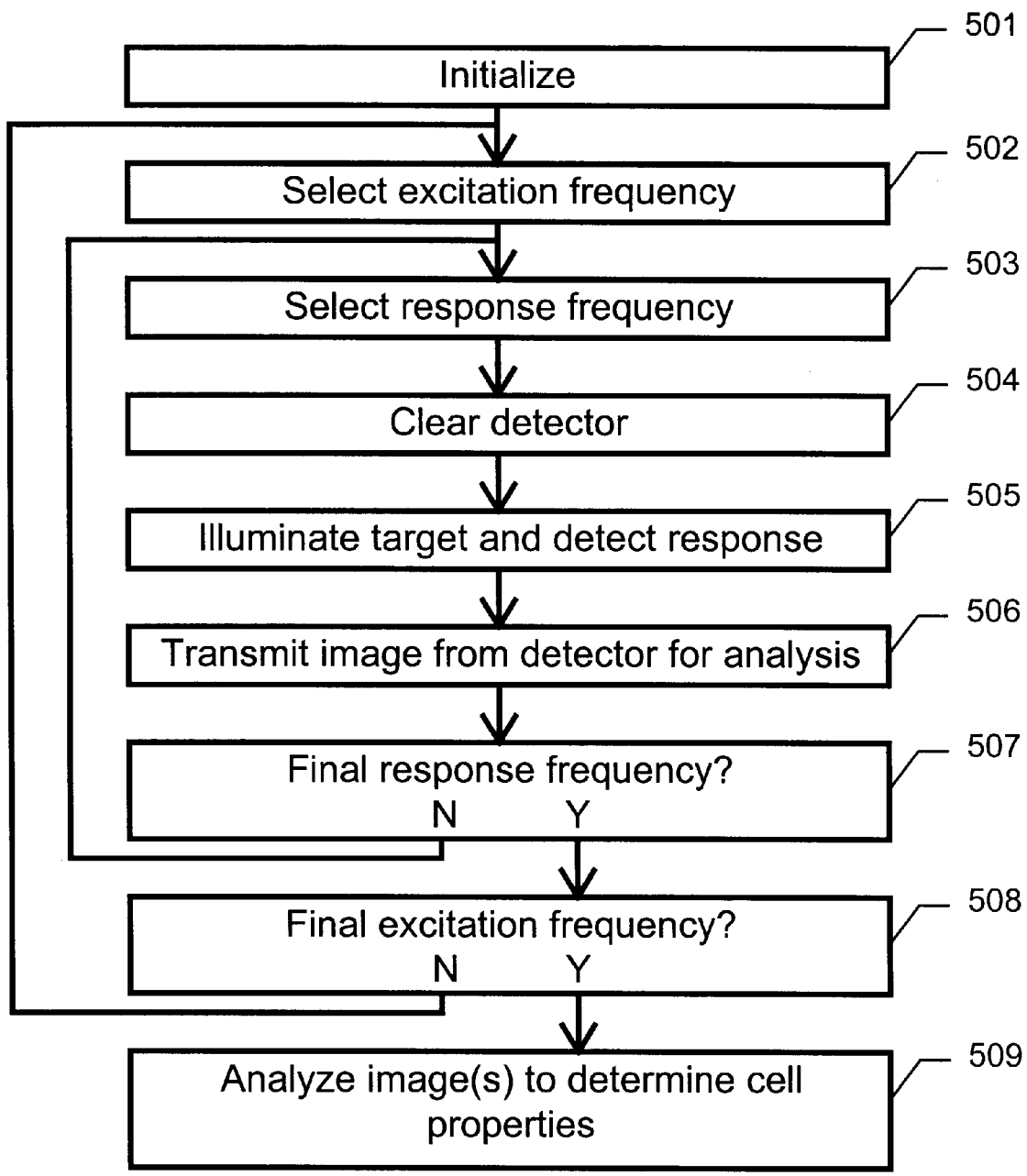
FIG. 5 is a flow diagram of the control of a multispectral imaging system according to the present invention.

FIG. 5 is a flow diagram of the control of a multispectral imaging system according to the present invention. Any parts of the system that need initialization are first initialized 501. An excitation wavelength is selected 502, for example by rotating a filter wheel. A response wavelength is selected 503, for example by rotating a filter wheel. The detector is cleared of any previous response information 504. The target is then illuminated with the selected excitation wavelength and the response at the selected response wavelength detected 505. The image from the detector of the target's response is transmitted for analysis 506. If this is not the final response wavelength to be detected 507, then a new response wavelength is selected 503 and the process repeated from there. If this is not the final excitation wavelength 507, then a new excitation wavelength is selected 502 and the process repeated from there. After all the response wavelength/excitation wavelength pairings have been detected, then the images are analyzed to determine the cell properties 509.

The particular sizes and equipment discussed above are cited merely to illustrate particular embodiments of the invention. It is contemplated that the use of the invention may involve components having different sizes and characteristics. It is intended that the scope of the invention be defined by the claims appended hereto.

We claim:

1. A method for determining properties of cells on a surface comprising:
   a) exposing said cells to a narrow band light beam;
   b) generating a broad band image corresponding to said surface comprising a broad band of light expressed by the cells in response to the narrow band light beam;
   c) generating a narrow band image corresponding to said broad band image and comprising the intensity of said broad band image in a narrow band; and
   d) determining the properties of the cells on the entire surface as a function of location on the surface from the narrow band image, where the step of exposing said cells to a narrow band light beam comprises generating a narrow band light beam; delivering the narrow band light beam to a sealed, remote probe; and delivering the narrow band light beam to the cells by the sealed probe.

2. A method for determining properties of cells on a surface comprising:
   a) exposing said cells to a narrow band light beam;
   b) generating a broad band image corresponding to said surface comprising a broad band of light expressed by the cells in response to the narrow band light beam;
   c) generating a narrow band image corresponding to said broad band image and comprising the intensity of said broad band image in a narrow band; and
   d) determining the properties of the cells on the entire surface as a function of location on the surface from the narrow band image, where the step of exposing said cells to a narrow band light beam comprises generating a narrow band light beam from a light source, and delivering the narrow band light beam to the cells by passing the narrow band light beam through a flexible light guide from the light source to a sealed, remote probe and then from the sealed, remote probe to the cells.

3. The method of claim 2, where the step of exposing said cells to a narrow band light beam comprises:
   a) generating a broad band light beam with a light source;
   b) filtering the broad band light beam to generate a narrow band light beam whose center wavelength varies with time;
   c) delivering the narrow band light beam to a probe; and
   d) delivering the narrow band light beam from the probe to the cells.

4. The method of claim 3, additionally comprising the step of filtering heat energy from the broad band light beam.

5. The method of claim 3, where the broad band light beam comprises light with wavelengths from approximately 200 nm to approximately 2000 nm, and comprises a total power of from approximately 10 mW/nm to approximately 800 mW/nm.

6. The method of claim 3, where the step of filtering the broad band light beam comprises passing the broad band light beam through a filter wheel, where the filter wheel comprises a plurality of filters, and rotating the filter wheel so that the broad band light beam passes through the filters in timed succession.

7. The method of claim 2, where the cells comprise a surface, and where the narrow band light beam is delivered to the cells so that energy from the narrow band light beam reaches the entire surface.

8. The method of claim 6, where the broad band collected light beam has a two dimensional cross section and where each point in the broad band collected light beam cross section corresponds to a point in the target surface.

9. The method of claim 8, where each signal in the plurality of signals comprises a multiple pixel cross section, and where each pixel in the multiple pixel cross section corresponds to a subset of the broad band collected light beam cross section.

10. The method of claim 2, where light is expressed by the target in a way chosen from the group consisting of: reflection, absorption, fluorescence, Raman scattering, diffuse scattering, and combinations thereof.

11. The method of claim 3, wherein:
   a) the step of generating a broad band light beam comprises energizing a Xenon arc lamp having a built-in parabolic reflector and providing approximately 40 mW/nm output power at wavelengths from approximately 250 nm to approximately 2200 nm;
   b) the step of filtering the broad band light beam comprises passing the broad band light beam through a first filter wheel, where the first filter wheel comprises a plurality of filters, and rotating the first filter wheel so that the broad band light beam passes through the filters in timed succession;
   c) the step of delivering a narrow band light beam to the target comprises passing the narrow band light beam through a flexible light guide from the light source to a sealed probe and then from the sealed probe to the target;
   d) the step of filtering the broad band collected light beam comprises passing the broad band collected light beam through a second filter wheel, where the second filter wheel comprises a plurality of filters, and rotating the second filter wheel so that the broad band light beam passes through the filters in timed succession; and
   e) the step of forming a plurality of signals comprises passing the narrow band collected light beams onto a device that outputs signals corresponding to the intensity of incident light.

12. An apparatus for determining properties of cells on a surface, comprising:
   a) source means for generating a narrow band light beam whose center wavelength varies with time;
   b) first transmission means for delivering the narrow band light beam to a sealed, remote probe;
   c) second transmission means for delivering the narrow band light beam from the probe to the cells;
   d) collection means for forming a collected light beam comprising a full image of said surface by collecting light expressed by the cells in response to the narrow band light beam;
   e) detector means for determining the spectral characteristics of said image and measuring a multispectral response of the cells by determining the intensity of said image at a first plurality of wavelengths at a plurality of points in said image, where the image information is preserved as a function of location; and
   f) analysis means for determining the cells' properties from spectral characteristics of said image.

13. The apparatus of claim 12, where the source means comprises an arc lamp and a parabolic reflector.

14. The apparatus of claim 12, where the transmission means comprises a liquid light guide.

15. The apparatus of claim 12, where the collection means comprises an imaging lens.

16. The apparatus of claim 12, where the detector means comprises a CCD array.

17. The apparatus of claim 12, additionally comprising control means for controlling the operation of the apparatus, where the control means comprises:
   a) means for selecting the center wavelength of the narrow band light beam; and
   b) means for selecting the first plurality of wavelengths.

* * * * *